(12) United States Patent
Cottard et al.

(10) Patent No.: US 7,458,993 B2
(45) Date of Patent: Dec. 2, 2008

(54) COMPOSITION USEFUL FOR THE OXIDATION DYEING OF HUMAN KERATINOUS FIBRES

(75) Inventors: Francois Cottard, Levallois-Perret (FR); Christine Rondeau, Sartrouville (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/603,815

(22) Filed: Jun. 26, 2003

(65) Prior Publication Data

US 2005/0015894 A1   Jan. 27, 2005

Related U.S. Application Data

(60) Provisional application No. 60/392,968, filed on Jul. 2, 2002.

(30) Foreign Application Priority Data

Jun. 26, 2002   (FR) .................................. 0207938

(51) Int. Cl.
*A61Q 5/10* (2006.01)
(52) U.S. Cl. .................. 8/405; 8/406; 8/410; 8/411; 8/421; 8/435; 8/581; 8/604
(58) Field of Classification Search ............ 5/405, 5/406, 410, 411, 421, 435, 581, 535, 604
See application file for complete search history.

(56) References Cited

U.S. PATENT DOCUMENTS 5,376,146 A * 12/1994 Casperson et al. ............. 8/408
6,004,355 A * 12/1999 Dias et al. ...................... 8/406
6,669,933 B2 * 12/2003 Duffer et al. ................ 424/70.1
2003/0028979 A1 * 2/2003 Duffer et al. .................... 8/406

FOREIGN PATENT DOCUMENTS

| DE | 41 35 760 | | 5/1993 |
| DE | 195 27 121 | A1 | 1/1997 |
| DE | 199 62 869 | | 6/2001 |
| GB | 2 033 939 | | 5/1980 |
| JP | 63-174917 | | 7/1988 |
| JP | 01-503064 | | 10/1989 |
| JP | 02-503000 | | 9/1990 |
| JP | 08-239313 | | 9/1996 |
| JP | 10-114635 | | 5/1998 |
| JP | 11-349456 | | 12/1999 |

OTHER PUBLICATIONS

D.F. Williams and W.H. Schmitt Ed.: "Chemistry and technology of the cosmetics and toiletries industry, 2nd edition, 1996", Blackie Academic and Professional (pp. 93-97).
R.C. Pepe et al. Ed.: "International cosmetic ingredient dictionary and handbook, 9$^{th}$ ed., 2002, vol. 2", The Cosmetic, Toiletry and Fragrance Association, USA (p. 1578).

* cited by examiner

*Primary Examiner*—Eisa B Elhilo
(74) *Attorney, Agent, or Firm*—Oblon, Spivak, McClelland, Maier & Neustadt, P.C.

(57) ABSTRACT

A composition useful for the oxidation dyeing of human keratinous fibers and in particular hair containing, in a cosmetically acceptable medium based on water and at a basic pH, at least one oxidation dye and an alkalinizing agent containing at least one alkali metal, alkaline-earth metal or ammonium metasilicate and at least one alkanolamine, and the dyeing method using this composition.

31 Claims, No Drawings

COMPOSITION USEFUL FOR THE OXIDATION DYEING OF HUMAN KERATINOUS FIBRES

REFERENCE TO PRIOR APPLICATIONS

This application claims priority to U.S. Provisional application 60/392,968, filed Jul. 2, 2002, and to French patent application 0207938, filed Jun. 26, 2002, both of which are incorporated herein by reference.

SUMMARY OF THE INVENTION

The invention relates to a composition useful for the oxidation dyeing of human keratinous fibres and in particular hair comprising, in a cosmetically acceptable medium based on water and at a basic pH, at least one oxidation dye and an alkalinizing agent comprising at least one alkali metal, alkaline-earth metal or ammonium metasilicate and at least one alkanolamine. Methods of making and using this composition also make up a part of the invention.

BACKGROUND OF THE INVENTION

It is known to dye human keratinous fibres and in particular hair with dyeing compositions containing oxidation dyes. Oxidation dyes comprise oxidation dye precursors and couplers.

Oxidation dye precursors, generally called oxidation bases, are colorless or weakly colored compounds which, combined with oxidizing products, can give rise to colored and dye compounds by a process of oxidative condensation. They are in particular ortho- or para-phenylene diamines, ortho- or para-aminophenols, or heterocyclic bases.

The shades obtained with these oxidation bases may be modified by combining the bases with couplers or color modifiers, the couplers being chosen in particular from aromatic meta-diamines, meta-aminophenols, meta-diphenols and certain heterocyclic compounds.

The variety of molecules used in oxidation bases and couplers allows a rich palette of colors to be obtained.

The oxidation dyeing method comprises applying to the fibres oxidation bases or a mixture of oxidation bases and couplers with an oxidizing agent, most often hydrogen peroxide, allowing them to act, and then rinsing the fibres. The application, which is generally carried out at a basic pH, makes it possible to obtain dyeing and simultaneously lightening of the fibre, which results in practice in the possibility of obtaining a final coloration which is lighter than the original color. In addition, the lightening of the fibre has the advantageous effect of generating a uniform color in the case of grey hair, and in the case of naturally pigmented hair, of making the color stand out, that is to say of making it more visible.

The lightening of hair is evaluated by the tone height which characterizes the degree or level of lightening. The notion of "tone" is based on the classification of natural shades, a tone separating each shade from the one immediately following it or preceding it. This definition and the classification of natural shades is well known to hair styling professionals and is published in the book "Sciences des traitements capillaires" [Science of hair treatment] by Charles ZVIAK, 1988, Ed. Masson, pp. 215 and 278.

The tone heights range from 1 (black) to 10 (light blonde), one unit corresponding to one tone; the higher the figure, the lighter the shade.

The lightening oxidation dyeing technology which has to make it possible to obtain sufficient lightening of the fibre and a covering of hair which is 100% white has up until now involved using either aqueous ammonia, or monoethanolamine, or a mixture of monoethanolamine and aqueous ammonia, as alkalinizing agent.

However, as everyone knows, aqueous ammonia has the major disadvantage of releasing an unpleasant odor during application of the dye.

Monoethanolamine, if used in high concentrations, sometimes causes irritations of the scalp in the form of pricklings.

Now, after major research studies carried out on the subject, the inventors have discovered that it is possible to reduce the unpleasant odor and the risks of scalp irritation of the dyes while obtaining the desired lightening level and intense colorations in varied shades, using, as alkalinizing agent, a mixture of at least one alkali metal or alkaline-earth metal or ammonium metasilicate and at least one alkanolamine.

DETAILED DESCRIPTION OF THE PREFERRED EMBODIMENTS

A first preferred embodiment of the invention is therefore a composition useful for the oxidation dyeing of human keratinous fibres and more particularly hair, comprising, in a cosmetically acceptable medium comprising water and having a basic pH, at least one oxidation dye and an alkalinizing agent, wherein the alkalinizing agent is a combination of at least one metasilicate selected from the group consisting of the group consisting of alkali metal, alkaline-earth metal or ammonium metasilicates and at least one alkanolamine.

The dyeing composition in accordance with the invention makes it possible to formulate less odorous and less irritating products and to reduce in particular the amount of alkanolamine conventionally used while the dyeing properties are perfectly maintained.

Another preferred embodiment of the invention is a method for the oxidation dyeing of human keratinous fibres and more particularly hair using the invention composition.

Another preferred embodiment of the invention is a ready-to-use composition for the oxidation dyeing of human keratinous fibres, and more particularly hair comprising the mixture of a composition described above and an oxidizing composition.

The expression "ready-to-use composition" is understood to mean, for the purposes of the invention, a composition intended to be applied as it is to keratinous fibres, that is to say that it can be stored as it is before use or can result from mixing two compositions immediately before use.

Alkalinizing Agent

The combination according to the invention of at least one alkali metal or alkaline-earth metal or ammonium metasilicate and at least one alkanolamine used as alkalinizing agent makes it possible to adjust the pH of the dyeing composition of the present invention from 7.2 to 13, and preferably from 8.5 to 11.5.

According to the present invention, the combination preferably comprises:

from 0.1 to 6% by weight approximately of one or more metasilicates, preferably from 0.5 to 5%, and more particularly from 1 to 3%, and, from 0.1 to 8% by weight approximately of one or more alkanolamines, preferably from 0.5 to 6%, and still more particularly from 1 to 5.5%, relative to the total weight of the composition.

The metasilicates useful herein include those selected from the group consisting of sodium, potassium or ammonium metasilicates. Preferably, sodium metasilicate is used (sodium metasilicate [$Na_2SiO_3$] is an anhydrous compound, but it can also exist in its hydrated forms with 5 or 9 molecules of water).

The alkanolamines useful herein include those selected from the group consisting of monoethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and trishydroxymethylaminomethane. Preferably, monoethanolamine is used.

The weight ratio anhydrous metasilicate/alkanolamine is advantageously comprised between 0.01 and 100, more particularly between 0.1 and 10, preferably between 0.2 and 2., including stated endpoints.

Medium

The cosmetically acceptable medium useful for dyeing in accordance with the invention comprises water and, optionally, at least one organic solvent. Typically the organic solvent is present for solubilizing compounds which might not be sufficiently soluble in water. Useful organic solvents include, for example, $C_1$-$C_4$ alkanols, such as ethanol and isopropanol; glycerol; polyols and polyol ethers such as propylene glycol, monomethyl ether of propylene glycol, monoethyl ether and monomethyl ether of diethylene glycol, and aromatic alcohols such as benzyl alcohol or phenoxyethanol, analogous products and mixtures thereof.

The solvent(s) may be present in proportions preferably ranging from 1 to 40% by weight approximately relative to the total weight of the dyeing composition, and still more preferably from 5 to 30% by weight approximately.

Oxidation Dyes

The oxidation dyes useful herein include those selected from the group consisting of oxidation bases and/or couplers.

Preferably, the compositions according to the invention contain at least one oxidation base.

The oxidation bases useful herein may be selected from the group consisting of those conventionally known in oxidation dyeing, and among which there may be mentioned in particular ortho- and para-phenylenediamines, double bases, ortho- and para-aminophenols, the following heterocyclic bases and their addition salts with an acid.

There may be mentioned in particular:
(I) the para-phenylenediamines of the following formula (I) and their addition salts with an acid:

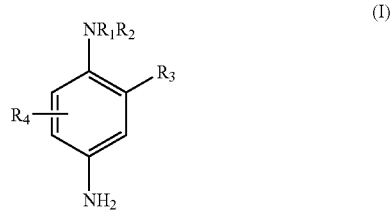

(I)

in which:
$R_1$ represents a hydrogen atom, a $C_1$-$C_4$ alkyl radical, a monohydroxy($C_1$-$C_4$ alkyl) radical, a polyhydroxy($C_2$-$C_4$ alkyl) radical, a ($C_1$-$C_4$)alkoxy($C_1$-$C_4$)alkyl radical, a $C_1$-$C_4$ alkyl radical substituted with a nitrogen-containing group, a phenyl radical or a 4'-aminophenyl radical;

$R_2$ represents a hydrogen atom, a $C_1$-$C_4$ alkyl radical, a monohydroxy($C_1$-$C_4$ alkyl) radical, a polyhydroxy($C_2$-$C_4$ alkyl) radical, a ($C_1$-$C_4$)alkoxy($C_1$-$C_4$)alkyl radical or a $C_1$-$C_4$ alkyl radical substituted with a nitrogen-containing group;

$R_1$ and $R_2$ may also form with the nitrogen atom carrying them a 5- or 6-membered nitrogen-containing heterocycle optionally substituted with one or more alkyl, hydroxyl or ureido groups;

$R_3$ represents a hydrogen atom, a halogen atom such as a chlorine atom, a $C_1$-$C_4$ alkyl radical, a sulpho radical, a carboxyl radical, a monohydroxy($C_1$-$C_4$ alkyl) radical, a hydroxy($C_1$-$C_4$ alkoxy) radical, an acetylamino($C_1$-$C_4$ alkoxy) radical, a mesylamino($C_1$-$C_4$ alkoxy) radical or a carbamoylamino($C_1$-$C_4$ alkoxy) radical;

$R_4$ represents a hydrogen or halogen atom or a $C_1$-$C_4$ alkyl radical.

Among the nitrogen-containing groups of formula (I) above, there may be mentioned in particular the amino, mono($C_1$-$C_4$)alkylamino, ($C_1$-$C_4$)dialkylamino, ($C_1$-$C_4$)trialkylamino, monohydroxy($C_1$-$C_4$)alkylamino, imidazolinium and ammonium radicals.

Among the para-phenylenediamines of formula (I) above, there may be mentioned more particularly para-phenylenediamine, para-tolylenediamine, 2-chloro-para-phenylenediamine, 2,3-dimethyl-para-phenylenediamine, 2,6-dimethyl-para-phenylene diamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, N-(4-aminophenyl)-3-hydroxypyrrolidine, and their addition salts with an acid.

Among the para-phenylenediamines of formula (I) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylene-diamine, 2,3-dimethyl-para-phenylenediamine, N,N-bis(β-hydroxyethyl)-para-phenylene-diamine, 2-chloro-para-phenylenediamine, and their addition salts with an acid.

(II) According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (II), and their addition salts with an acid:

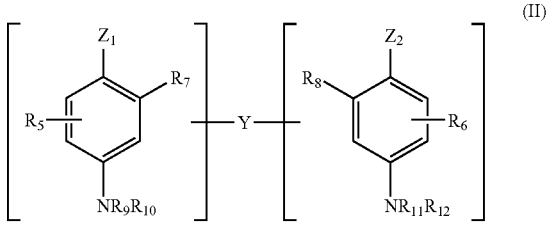

in which:
- $Z_1$ and $Z_2$, which are identical or different, represent a hydroxyl or —$NH_2$ radical which may be substituted with a $C_1$-$C_4$ alkyl radical or with a linking arm Y;
- the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or $C_1$-$C_6$ alkoxy radicals;
- $R_5$ and $R_6$ represent a hydrogen or halogen atom, a $C_1$-$C_4$ alkyl radical, a monohydroxy($C_1$-$C_4$ alkyl) radical, a polyhydroxy($C_2$-$C_4$ alkyl) radical, an amino($C_1$-$C_4$ alkyl) radical or a linking arm Y;
- $R_7$, $R_8$, $R_9$, $R_{10}$, $R_{11}$ and $R_{12}$, which are identical or different, represent a hydrogen atom, a linking arm Y or a $C_1$-$C_4$ alkyl radical;

it being understood that the compounds of formula (II) contain only one linking arm Y per molecule.

Among the nitrogen-containing groups of formula (II) above, there may be mentioned in particular the amino, mono($C_1$-$C_4$)alkylamino, ($C_1$-$C_4$)dialkylamino, ($C_1$-$C_4$)trialkylamino, monohydroxy($C_1$-$C_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

(III) The para-aminophenols corresponding to the following formula (III), and their addition salts with an acid:

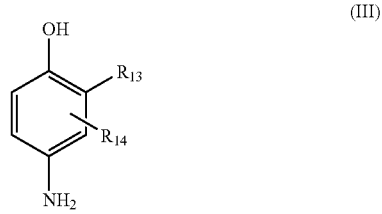

in which:

$R_{13}$ represents a hydrogen atom, or a halogen atom such as fluorine, a $C_1$-$C_4$ alkyl, monohydroxy($C_1$-$C_4$ alkyl), ($C_1$-$C_4$)alkoxy($C_1$-$C_4$)alkyl, amino($C_1$-$C_4$ alkyl) or hydroxy ($C_1$-$C_4$)alkylamino($C_1$-$C_4$ alkyl) radical, $R_{14}$ represents a hydrogen atom, or a halogen atom such as fluorine, a $C_1$-$C_4$ alkyl, monohydroxy($C_1$-$C_4$ alkyl), polyhydroxy($C_2$-$C_4$ alkyl), amino($C_1$-$C_4$ alkyl), cyano ($C_1$-$C_4$ alkyl) or ($C_1$-$C_4$)alkoxy($C_1$-$C_4$)alkyl radical.

Among the para-aminophenols of formula (III) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethyl-phenol, 4-amino-2-methoxymethylphenol, 4-amino-2-aminomethylphenol, 4-amino-2-(β-hydroxyethylaminomethyl)phenol, and their addition salts with an acid.

(IV) The ortho-aminophenols which can be used as oxidation bases in the context of the present invention are chosen in particular from 2-aminophenol, 2-amino-1-hydroxy-5-methylbenzene, 2-amino-1-hydroxy-6-methylbenzene, 5-acetamido-2-amino-phenol, and their addition salts with an acid.

(V) Among the heterocyclic bases which can be used as oxidation bases in the dyeing compositions in accordance with the invention, there may be mentioned more particularly pyridine derivatives, pyrimidine derivatives, pyrazole derivatives, and their addition salts with an acid.

Among the pyridine derivatives, there may be mentioned more particularly the compounds described, for example, in Patents GB 1,026,978 and GB 1,153,196, such as 2,5-diaminopyridine, 2-(4-methoxyphenyl)amino-3-aminopyridine, 2,3-diamino-6-methoxy-pyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described, for example, in Patents DE 2 359 399; JP 88-169 571; JP 91-10659 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application FR-A-2 750 048 and among which there may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo [1,5-a]pyrimidine-3,5-diamine; 3-aminopyrazolo[1,5-a]pyrimidin-7-ol; 3-amino-pyrazolo[1,5-a]pyrimidin-5-ol; 2-(3-aminopyrazolo[1,5-a]pyrimidin-7-ylamino)ethanol, 2-(7-amino-pyrazolo[1,5-a]pyrimidin-3-ylamino)ethanol, 2-[(3-aminopyrazolo[1,5-a]pyrimidin-7-yl)-(2-hydroxyethyl) amino]ethanol, 2-[(7-aminopyrazolo[1,5-a]pyrimidin-3-yl)-(2-hydroxy-ethyl)amino]ethanol, 5,6-dimethylpyrazolo[1,5-a]pyrimidine-3,7-diamine, 2,6 -dimethylpyrazolo[1,5-a] pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, their addition salts and their tautomeric forms, when a tautomeric equilibrium exists and their addition salts with an acid.

Among the pyrazole derivatives, there may be mentioned more particularly the compounds described in Patents DE 3 843 892, DE 4 133 957 and Patent Applications WO 94/08969, WO 94/08970, FR-A-2 733 749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3 -methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

According to the present invention, the oxidation bases preferably represent from 0.0005 to 12% by weight approximately of the total weight of the composition, and still more preferably from 0.005 to 8% by weight approximately of this weight.

The couplers which can be used in the dyeing composition according to the invention include those conventionally used in oxidation dyeing compositions, that is to say meta-aminophenols, meta-phenylenediamines, meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and their addition salts with an acid.

These couplers are more particularly selected from the group consisting of 2,4-diamino-1-(β-hydroxyethyloxy)benzene, 2-methyl-5-aminophenol, 5-N-(β-hydroxyethyl)amino-2-methylphenol, 3-aminophenol, 2-chloro-3-amino-6-methylphenol, 1,3-dihydroxy-benzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diamino-phenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole and their addition salts with an acid.

When they are present, these couplers preferably represent from 0.0001 to 10% by weight approximately of the total weight of the composition, and still more preferably from 0.005 to 5% by weight approximately.

In general, the addition salts with an acid of the oxidation bases and couplers are chosen in particular from the hydrochlorides, hydrobromides, sulphates, tartrates, lactates and acetates.

The composition according to the invention may also contain, in addition to the oxidation dyes defined above, direct dyes for enriching the shades with glints. These direct dyes may then be chosen in particular from neutral, cationic or anionic nitro, azo or anthraquinone dyes in the proportion by weight of about 0.001 to 20%, and preferably 0.01 to 10% of the total weight of the composition.

Adjuvants

The dyeing composition in accordance with the invention may also contain various adjuvants including as those which are conventionally used in hair dyeing compositions. Included are anionic, cationic, nonionic, amphoteric or zwitterionic surfactants or mixtures thereof, fatty alcohols, fatty acids, anionic, cationic, nonionic, amphoteric or zwitterionic polymers or mixtures thereof, inorganic or organic thickening agents or thickening polymers such as, for example, nonionic guar gums, associative polymers containing at least one hydrophilic unit and at least one fatty chain and of a nonionic, anionic, cationic or amphoteric nature, antioxidants or reducing agents, penetrating agents, sequestering agents such as EDTA and etidronic acid, UV-screening agents, waxes, perfumes, buffers, dispersing agents, conditioning agents such as, for example, modified or unmodified, volatile or nonvolatile silicones, film-forming agents, pearlescent agents, preservatives, ceramides, pseudoceramides, vegetable, mineral or synthetic oils, vitamins or provitamins such as panthenol, opacifiers, and the like.

Preferably, the dyeing composition of the invention comprises at least one cationic polymer in the proportion of about 0.05 to 10% by weight, and at least one surfactant, which is preferably nonionic, in the proportion of 0.1 to 20% by weight, relative to the total weight of the composition.

Preferably, it also contains at least one thickening polymer preferably selected from the group consisting of associative polymers in the proportion of about 0.05 to 10% by weight relative to the total weight of the composition.

The reducing agents or antioxidants may be chosen in particular from sodium sulphite, thioglycolic acid and thiolactic acid and their salts of ammonium, sodium bisulphite, dehydroascorbic acid, hydroquinone, 2-methylhydroquinone, tert-butylhydroquinone, homogentisic acid, and they are then generally present in quantities ranging from about 0.05 to 3% by weight relative to the total weight of the composition.

The dyeing composition of the invention may also comprise aqueous ammonia. More particularly, the amount of aqueous ammonia in the dyeing composition is of at most 2% by weight (aqueous solution of gaseous ammonia at 20% by weight) relative to the total weight of the composition.

Of course, persons skilled in the art will be careful to choose this or these possible additional compounds such that the advantageous properties intrinsically attached to the dyeing composition in accordance with the invention are not, or not substantially, impaired by the addition(s) envisaged.

The dyeing method according to the invention preferably comprises the following steps: at the time of use, a dyeing composition as described above and therefore comprising, in a cosmetically acceptable medium based on water and at a basic pH ranging from 7.2 to 13, at least one oxidation dye and a combination of metasilicate(s) and alkanolamine(s) according to the invention, is mixed with an oxidizing composition, the mixture obtained is then applied to the keratinous fibres, it is allowed to act for, for example, 3 to 50 minutes approximately, preferably 5 to 30 minutes approximately, after which the keratinous fibres are rinsed, washed with shampoo, rinsed again and dried.

The dyeing composition, before mixing with the oxidant, may be in various forms, such as a liquid, cream or gel form, optionally pressurized or in any other form appropriate for carrying out, after mixing, a dyeing of human keratinous fibres and in particular hair.

Oxidant

In the oxidizing composition, the oxidizing agent is preferably selected from the group consisting of hydrogen peroxide and compounds capable of releasing hydrogen peroxide in situ, oxidoreduction enzymes such as laccases, peroxidases and oxidoreductases containing 2 electrons (such as uricase), where appropriate in the presence of their respective donor or cofactor.

The use of hydrogen peroxide is particularly preferred. This oxidizing agent advantageously consists of a solution of hydrogen peroxide whose titre may vary, more particularly, from about 1 to 40 volumes, and still more preferably from about 5 to 40.

According to a particular embodiment of the invention, the weight ratio dyeing composition/oxidizing composition is comprised between 2/1 and 1/6, preferably between 1/1 and 1/3.

The examples which follow are intended to illustrate the invention without, however, exhibiting a limiting character.

EXAMPLES 1-3

The following dyeing compositions were prepared:
(amounts expressed in grams of active substance)

|  | Example 1 | Example 2 | Example 3 |
|---|---|---|---|
| Para-phenylenediamine | 0.24 | 0.24 | 0.24 |
| Para-aminophenol | 0.44 | 0.44 | 0.44 |
| 2-aminophenol | 0.028 | 0.028 | 0.028 |
| 1,3-dihydroxybenzene | 0.192 | 0.192 | 0.192 |
| 3-aminophenol | 0.019 | 0.019 | 0.019 |
| 5-N-(β-hydroxyethyl)amino-2-methylphenol | 0.021 | 0.021 | 0.021 |
| 1,3-dihydroxy-2-methylbenzene | 0.055 | 0.055 | 0.055 |
| Anhydrous sodium metasilicate | 2 | 2 | 2 |
| Monoethanolamine | 5.45 | 5.45 | 5.45 |
| Reducing agent, antioxidant, sequestrant, perfume | q.s. | q.s. | q.s. |
| Propylene glycol | 10 | 10 | 10 |
| Anionic polymer: crosslinked polyacrylic acid | 0.4 | 0.4 | 0.4 |
| Amphoteric polymer: Polyquaternium 22 (C.T.F.A. name) Merquat 280 sold by the company ONDEO | 1.5 | 1.5 |  |
| Cationic polymer: Polyquaternium 6 (C.T.F.A name) Merquat 100 sold by the company ONDEO |  |  | 2.8 |
| Cationic polymer: Hexadimethrine Chloride (C.T.F.A. name) Mexomer PO sold by the company CHIMEX | 3 | 3 |  |
| Anionic surfactant: powdered sodium lauryl sulphate | 3 |  |  |
| Nonionic surfactant: oxyethylenated lauryl alcohol containing 12 mol of ethylene oxide |  | 7.5 | 7.5 |
| Nonionic surfactant: oxyethylenated oleocetyl alcohol containing 30 mol of ethylene oxide |  | 4 | 4 |
| Nonionic surfactant: oxyethylenated decyl alcohol containing 3 mol of ethylene oxide | 10 | 10 | 10 |
| Nonionic surfactant: oxyethylenated decyl alcohol containing 5 mol of ethylene oxide | 8 |  |  |
| Lauric acid | 2.5 | 2.5 | 2.5 |
| Cetylstearyl alcohol 50/50 | 11.5 | 11.5 | 11.5 |
| Pearlescent agent: hydrophobic pyrogenic silica | 1.2 | 1.2 | 1.2 |
| Pearlescent agent: glyceryl monostearate | 2 | 2 | 2 |
| Demineralized water qs | 100 | 100 | 100 |

At the time of use, each dyeing composition described above is mixed weight for weight with a solution of hydrogen peroxide at 20 volumes (6% by weight).

The mixtures thus prepared were applied for 30 minutes to locks of natural or permanently waved grey hair which is 90% white. The locks were then rinsed, washed with a standard shampoo, rinsed again and then dried.

It was observed that these mixtures were a lot less odorous than those of the prior art with satisfactory application qualities.

The hair was dyed in a golden blonde shade for each of Examples 1 to 3.

Compared with prior art compositions which are identical except that they do not contain sodium metasilicate and have a much higher content of monoethanolamine (of the order of 10% by weight of the dyeing composition), the dyeing performances of compositions 1 to 3 were preserved.

As used herein, the term "approximately" preferably means +/−10%. The phrase "between X and Y" includes X and Y.

The above description of the invention sets forth the manner and process of making and using it such that it enables any person skilled in this art to make and use the same, specifically including the making and using of the following preferred embodiments and those set out in the claims, all of which make up a part of this description:

a composition for the oxidation dyeing of human keratinous fibres and more particularly hair, comprising, in a cosmetically acceptable medium based on water and at a basic pH, at least one oxidation dye and an alkalinizing agent, wherein the alkalinizing agent is a combination of at least one metasilicate selected from the group consisting of the group consisting of alkali metal, alkaline-earth metal or ammonium metasilicates and at least one alkanolamine, and a method for dyeing human keratinous fibres and in particular hair, wherein, at the time of use, an invention dyeing composition as described herein is mixed with an oxidizing composition, in that the mixture obtained is applied to the fibres, it is allowed to act for 3 to 50 minutes, preferably 5 to 30 minutes, after which the fibres are rinsed, washed with shampoo, rinsed again and dried, the oxidizing composition comprising hydrogen peroxide or a compound capable of releasing hydrogen peroxide in situ, or an oxidoreduction enzyme.

All references, documents, brochures, texts, articles, patents, applications, etc. mentioned above are incorporated herein by reference. Where a numerical limit or range is stated, all values and subranges within these stated ranges or limits are expressly included as if specifically written out.

The invention claimed is:

1. A composition comprising, in a cosmetically acceptable medium comprising water and having a basic pH, at least one oxidation dye and an alkalinizing agent, wherein the alkalinizing agent comprises at least one metasilicate selected from the group consisting of alkali metal, alkaline-earth metal and ammonium metasilicates and at least one alkanolamine, wherein the weight ratio of metasilicate to alkanolamine is between 0.1 and 2.

2. The composition according to claim 1, comprising sodium metasilicate.

3. The composition according to claim 1, wherein the alkanolamine is selected from the group consisting of monoethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-pr-opanediol, 3-amino-1,2-propanediol, 3-dimethylamino-1,2-propanediol and trishydroxy-methylaminomethane.

4. The composition according to claim 1, comprising monoethanolamine.

5. The composition according to claim 1, wherein the alkalinizing agent comprises from 0.1 to 6% by weight of metasilicate relative to the total weight of the composition.

6. The composition according to claim 5, wherein the alkalinizing agent comprises from 0.5 to 5% by weight of metasilicate relative to the total weight of the composition.

7. The composition according to claim 6, wherein the alkalinizing agent comprises from 1 to 3% by weight of metasilicate relative to the total weight of the composition.

8. The composition according to claim 1, wherein the alkalinizing agent comprises from 0.1 to 8% by weight of alkanolamine relative to the total weight of the composition.

9. The composition according to claim 8, wherein the alkalinizing agent comprises from 0.5 to 6% by weight of alkanolamine relative to the total weight of the composition.

10. The composition according to claim 9, wherein the alkalinizing agent comprises from 1 to 5.5% by weight of alkanolamine relative to the total weight of the composition.

11. The composition according to claim 1, wherein its pH is from 7.2 to 13.

12. The composition according to claim 11, wherein its pH is from 8.5 to 11.5.

13. The composition according to claim 1, wherein the oxidation dye is selected from the group consisting of oxidation bases and couplers.

14. The composition according to claim 13, comprising at least one oxidation base.

15. The composition according to claim 14, wherein the oxidation base is selected from the group consisting of ortho- and para-phenylenediamines, double bases, ortho- and para-aminophenols, heterocyclic bases and their addition salts with an acid.

16. The composition according to claim 13, comprising at least one coupler selected from the group consisting of meta-aminophenols, meta-phenylenediamines, meta-diphenols, naphthols, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and their addition salts with an acid.

17. The composition according to claim 15, wherein the addition salts with an acid are selected from the group consisting of the hydrochlorides, hydrobromides, sulphates, tartrates, lactates and acetates.

18. The composition according to claim 16, wherein the addition salts with an acid are selected from the group consisting of the hydrochlorides, hydrobromides, sulphates, tartrates, lactates and acetates.

19. The composition according to claim 14, wherein the at least one oxidation base is present at a concentration ranging from 0.0005 to 12% by weight relative to the total weight of the composition.

20. The composition according to claim 13, comprising at least one coupler.

21. The composition according to claim 20, wherein the at least one coupler is present at a concentration between 0.0001 and 10% by weight relative to the total weight of the composition.

22. The composition according to claim 1, wherein the cosmetically acceptable medium further comprises at least one organic solvent.

23. The composition according to claim 22, wherein the at least one organic solvent is present in a proportion ranging from 1 to 40% by weight relative to the total weight of the composition.

24. The composition according to claim 1, further comprising at least one cationic polymer in a proportion of 0.05 to 10% by weight relative to the total weight of the composition, and further comprising at least one nonionic surfactant in a proportion of 0.1 to 20% by weight relative to the total weight of the composition.

25. A ready-to-use composition comprising the composition of claim 1.

26. The composition according to claim 25, wherein the composition comprises hydrogen peroxide.

27. The composition according to claim 1, wherein the weight ratio of metasilicate to alkanolamine is between 0.2 and 2.

28. A method for dyeing human keratinous fibres comprising: mixing a composition comprising, in a cosmetically acceptable medium comprising water and having a basic pH, at least one oxidation dye and an alkalinizing agent, wherein the alkalinizing agent comprises at least one metasilicate selected from the group consisting of alkali metal, alkaline-earth metal and ammonium metasilicates and at least one alkanolamine, with an oxidizing composition; and applying the mixture obtained to the fibres, after which the fibres are rinsed, washed with shampoo, rinsed again and dried, the oxidizing composition comprising hydrogen peroxide or a compound capable of releasing hydrogen peroxide in situ, or an oxidoreduction enzyme.

29. The method of claim 28, wherein the mixture applied to the fibers is allowed to act on the fibers for 3 to 50 minutes before rinsing.

30. The method of claim 28, wherein the mixture applied to the fibers is allowed to act on the fibers for 5 to 30 minutes before rinsing.

31. The method of claim 28, wherein said fibers are human hair.

* * * * *